United States Patent
Rodkey et al.

(10) Patent No.: US 7,904,208 B1
(45) Date of Patent: Mar. 8, 2011

(54) COMPUTER INSTRUCTIONS FOR CENTRALIZED MANAGEMENT OF A HYDROGEN GENERATION NETWORK

(75) Inventors: Ryan Scott Rodkey, Sugar Land, TX (US); John Frank Rodkey, Jr., Missouri City, TX (US); Mark Stephen Ledder, Fredricksburg, TX (US); David Lynn Hickey, Rosharon, TX (US); Darren Lynn Ross, Sugar Land, TX (US); Ronald F. Ramsey, St. Petersburg, FL (US)

(73) Assignee: Tech Radium, Inc., Sugar Land, TX (US)

( * ) Notice: Subject to any disclaimer, the term of this patent is extended or adjusted under 35 U.S.C. 154(b) by 879 days.

(21) Appl. No.: 11/837,319

(22) Filed: Aug. 10, 2007

(51) Int. Cl.
| | |
|---|---|
| G05B 21/00 | (2006.01) |
| G05D 3/12 | (2006.01) |
| G05D 5/00 | (2006.01) |
| G05D 9/00 | (2006.01) |
| G05D 11/00 | (2006.01) |
| G05D 17/00 | (2006.01) |
| C01B 3/00 | (2006.01) |
| C01B 6/00 | (2006.01) |

(52) U.S. Cl. ......... 700/266; 700/287; 700/291; 700/297; 252/188.25

(58) Field of Classification Search .......... 700/266, 700/286–287, 291, 297; 252/188.1, 188.25, 252/188.26

See application file for complete search history.

(56) References Cited

U.S. PATENT DOCUMENTS

| | | | |
|---|---|---|---|
| 5,228,529 A * | 7/1993 | Rosner ............... 180/65.225 |
| 5,300,369 A * | 4/1994 | Dietrich et al. ............ 429/7 |
| 5,643,352 A * | 7/1997 | Werth ................. 75/255 |
| 6,332,434 B1 * | 12/2001 | De Souza et al. .......... 123/3 |
| 6,336,430 B2 * | 1/2002 | de Souza et al. .......... 123/3 |
| 6,442,241 B1 | 8/2002 | Tsumpes |
| 6,463,462 B1 | 10/2002 | Smith |
| 6,496,568 B1 | 12/2002 | Nelson |
| 6,643,355 B1 | 11/2003 | Tsumpes |
| 6,678,358 B2 | 1/2004 | Langsenkamp et al. |
| 6,683,870 B1 | 1/2004 | Archer |
| 6,697,477 B2 | 2/2004 | Fleischer |
| 6,697,951 B1 * | 2/2004 | Sinha et al. ........... 713/300 |
| 6,786,245 B1 * | 9/2004 | Eichelberger et al. ...... 141/4 |
| 6,816,878 B1 | 11/2004 | Zimmers et al. |
| 6,871,214 B2 | 3/2005 | Parsons |
| 6,912,462 B2 | 6/2005 | Ogaki |
| 6,931,415 B2 | 8/2005 | Nagahara |
| 6,973,166 B1 | 12/2005 | Tsumpes |
| 7,463,986 B2 * | 12/2008 | Hayes ................ 702/62 |
| 7,471,010 B1 * | 12/2008 | Fingersh ............... 290/55 |
| 2002/0032020 A1 | 3/2002 | Brown |
| 2004/0086768 A1 * | 5/2004 | Fleckner et al. .......... 429/38 |
| 2005/0013417 A1 | 1/2005 | Zimmers et al. |
| 2007/0156257 A1 * | 7/2007 | Peters ................ 700/22 |
| 2007/0259220 A1 * | 11/2007 | Redmond ............. 429/12 |
| 2008/0231836 A1 * | 9/2008 | Curello et al. .......... 356/72 |
| 2008/0272934 A1 * | 11/2008 | Wang et al. ........ 340/870.11 |
| 2009/0076661 A1 * | 3/2009 | Pearson et al. .......... 700/291 |

\* cited by examiner

*Primary Examiner* — Ramesh B Patel

(57) ABSTRACT

Computer instructions in communication with at least one processor having data storage. The processor is in communication with a hydrogen generation network. The computer instructions instruct the processor to form a dynamic information database in the data storage, receive and store at least one hydrogen generating device identification and/or discretionary power consumption information, and receive and store dispatchable power source information and/or non-dispatchable power source information. The computer instructions instruct the processor to receive at least one message input using an administrator interface and transmit the message to the hydrogen generation network. The computer instructions instruct the processor to receive at least one response from the hydrogen generation network for regulating hydrogen production and store the response in the dynamic information database.

20 Claims, 3 Drawing Sheets

COMPUTER INSTRUCTIONS FOR CENTRALIZED MANAGEMENT OF A HYDROGEN GENERATION NETWORK

FIELD

The present embodiments relate generally to computer instructions for minimizing risk of explosion by enabling centralized communication with a decentralized hydrogen generation network for managing power from a plurality of power sources, such as wind, solar, and hydrocarbon-based sources for balanced power distribution to hydrogen generating devices.

BACKGROUND

Hydrogen generation networks require enhanced safety and security while fulfilling their power consumption needs, due to the potential dangers and difficulties posed by the storage and production of hydrogen.

There exists a need for computer instructions to perform a centralized method for monitoring and managing decentralized hydrogen generation networks to promote efficiency and avoid safety hazards presented by hydrogen.

A need exists for a computerized system and method for automating and delivering messages concerning power availability to owners and users of hydrogen generation networks, which include messages to facility managers, individuals, vendors, and others.

A need exists for a computerized system and method that can be used in the face of a major hurricane or other natural disaster to regulate and inform owners and operators of hydrogen generation networks concerning power availability and users of hydrogen generation networks concerning hydrogen availability.

A need exists for a computerized method for using digital information and responses to bridge the gap between the government or other administrative persons and the public by simultaneously communicating power availability with individuals and users, which can include hospitals, fire stations, and first responders, without being limited to one communication device or one message.

A need exists for a computerized method of communication from an administrator which reaches all possible forms of communication devices, so that all members of a power management network can be reached in multiple languages using multiple devices.

The present embodiments meet these needs.

BRIEF DESCRIPTION OF THE DRAWINGS

The detailed description will be better understood in conjunction with the accompanying drawings as follows.

Figure 1:
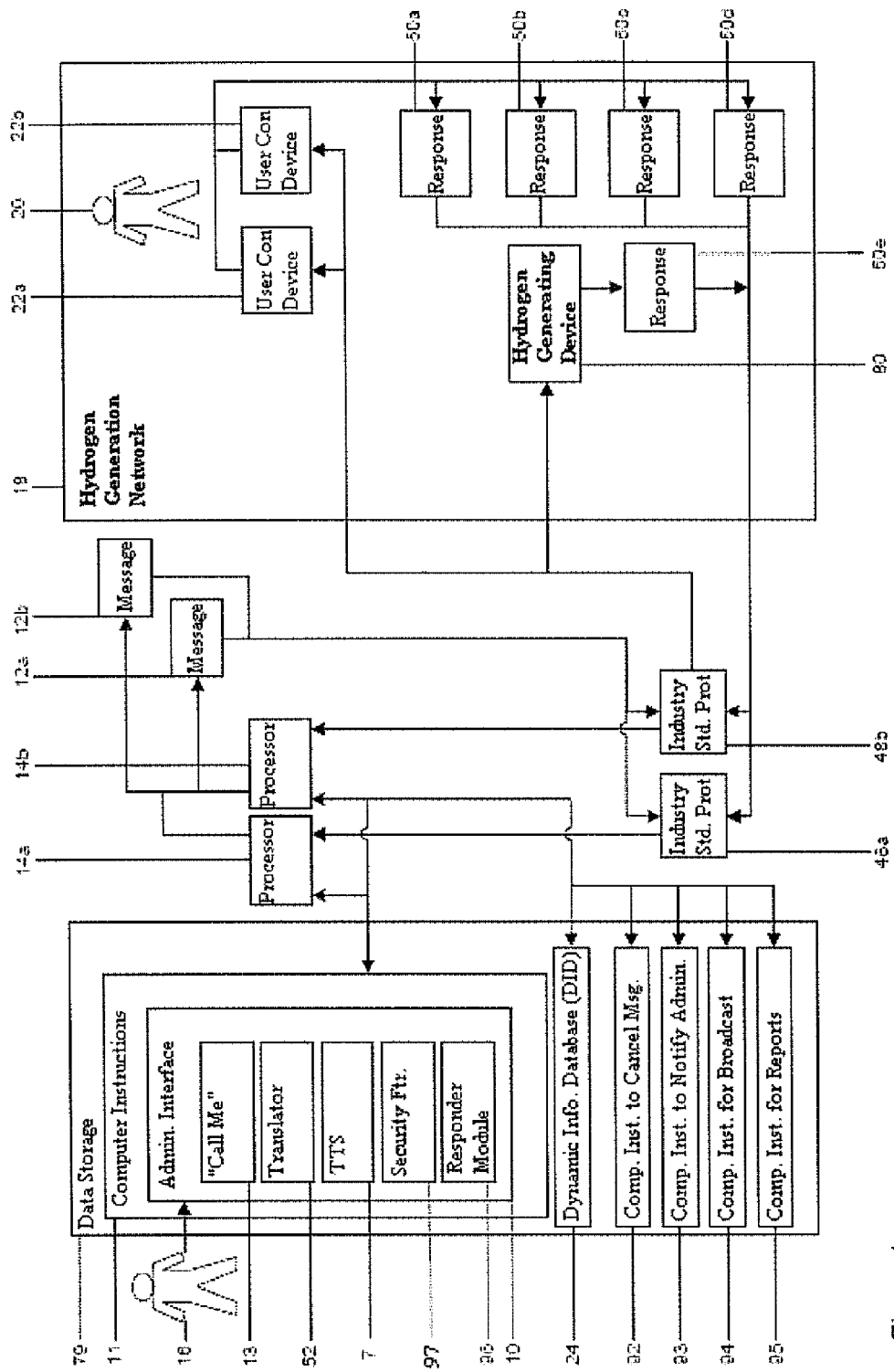
FIG. 1 depicts a representation of an embodiment of a digital notification and response system useable for handling power management.

The present embodiments are detailed below with reference to the listed Figures.

DETAILED DESCRIPTION OF THE EMBODIMENTS

Before explaining the present embodiments in detail, it is to be understood that the embodiments are not limited to the particular embodiments and that the invention can be practiced or carried out in various ways.

The present embodiments relate to computer instructions for performing a method for minimizing risk of explosion by centralized communication with a decentralized hydrogen generation network to regulate hydrogen production by at least one hydrogen generating device.

The present computer instructions provide improved safety over conventional management of hydrogen generation networks through use of an immediate response information system or emergency system, which can be used during brown outs, periods of high energy demand, and periods where a natural disaster, such as a storm, has destroyed or limited the capacity of energy-providing infrastructure.

The present embodiments relate to computer instructions for creating and delivering messages, routing messages, and verifying and collecting responses to the messages for hydrogen generation networks or owners or users hydrogen generation networks relating to power availability, allowing for secure and efficient, real-time, instantaneous management of power directed to one or more hydrogen generating devices.

The present embodiments are universally applicable to any type of messaging system and device used by message recipients.

The present computer instructions are contemplated to be in communication with at least one processor, such as resident on data storage in communication with a processor directly, or in communication over one or more networks. The processor is contemplated to be in communication with a hydrogen generation network containing one or more hydrogen generating devices, such as supplemental hydrogen generators, electrolysis-water hydrogen generators, electrolyte-water hydrogen generator, or combinations thereof. One or more hydrogen generating devices can include a hydrogen generating device processor and a hydrogen generating device identification code. One or more hydrogen generating devices can also include a controller, such as a software program that uniquely manages power consumption and transmission information for specific users of the hydrogen generating device, a controller identification code, such as a number like 4511-Dacoma, or combinations thereof.

The present computer instructions instruct a processor to form a dynamic information database in data storage, which can include any type of computer memory, such as a hard drive, a remote server, flash memory, and similar data storage mediums. The computer instructions also instruct the processor to receive and store identifications for one or more hydrogen generating devices, discretionary power consumption information for one or more hydrogen generating devices, or combinations thereof in the dynamic information database. Discretionary power consumption information can include an amount of power that the associated hydrogen generating device requires during a specified time interval.

The present computer instructions can further instruct a processor to receive and store dispatchable and non-dispatchable power source information relating to one or more dispatchable or non-dispatchable power sources in the dynamic information database. Power source information can include the capacity of each power source, the availability of power, and other similar information.

Dispatchable power sources can include hydroelectric power plants, hydrocarbon based electrical production facilities, nuclear power plants, geothermal power generation facilities, one or more banks of batteries, capacitors, or fuel cells, an ocean powered facilities using tidal power, or combinations thereof.

Non-dispatchable power sources can include wind power facilities, solar powered facilities, ocean powered facilities using wave height, currents, or combinations thereof, intermittent water supply hydroelectric facilities, or combinations thereof.

In a contemplated embodiment, the computer instructions can also instruct a processor to receive a location for one or more hydrogen generating devices and store the location in the dynamic information database. The hydrogen generating device location can be a physical address, an electronic address such as an internet protocol (IP) address, or combinations thereof.

The present computer instructions further instruct a processor to receive one or more messages input using an administrator interface in communication with the processor and one or more dispatchable or non-dispatchable power sources.

The administrator interface can be a computer, a cellular telephone, a personal digital assistant, or other similar devices able to input data, messages, and commands into a processor. The administrator interface can also be a local area network interface, a wide area network interface, a virtual private network interface, a synchronous transfer mode interface, a synchronous optical network interface, a call center, a voice mail, or another similar means to transmit messages to numerous contacts.

The administrator interface can be operated by an administrator, such as a dispatchable power supplier, a non-dispatchable power supplier, a government agency, a entity responsible for coordinating dispatchable and non-dispatchable power to hydrogen generating devices, a processor associated with the dynamic information database, another digital notification and response system, an analog notification system, and combinations thereof.

The computer instructions further instruct the processor to transmit one or more messages to the hydrogen generation network through at least one industry standard protocol. It is contemplated that the messages can be used for activating or deactivating hydrogen generating devices, managing decentralized storage of hydrogen, or combinations thereof.

The messages can include predefined messages, custom messages, or combinations thereof. The messages can also include audio files, such as MP3 files, MP4 files, WAV files, AIFF files, AVI files, or ACC files, image files, such as BMP or JPG files, video files, such as H.264 Mpeg files, text files, electronic signals, such as radio transmissions, or combinations thereof. It is contemplated that audio files can be transmitted via e-mail, phone, a link on a website, or combinations thereof.

It is contemplated that messages can be transmitted through any number of industry standard protocols individually or simultaneously. Industry standard protocols can include a Megaco/H.248 protocol, simple message transfer protocol (SMTP), a short message service (SMS) protocol, a multimedia message service (MMS) protocol, an enhanced message service (EMS) protocol, a media gateway control protocol (MGCP), a SIP protocol, a H.323 protocol, an ISDN protocol, a PSTN protocol, and combinations thereof.

It is also contemplated that messages and responses can be transmitted simultaneously to multiple devices of a single individual, over one or multiple networks, in multiple languages.

The present computer instructions can instruct a processor to convert messages from text to a sound file, such as through use of a text-to-sound file converter, such as a Real Speak text-to-sound converter, of Burlington, Mass. USA. Use of a text-to-sound file converter is beneficial for ensuring recognition of messages upon arrival, because the one or more messages remain consistent through delivery by the same voice, with the same accent, dynamic, and delivery speed. Additionally, use of a text-to-sound file converter enables individuals with disabilities, namely visual impairment, to also receive messages.

For example, the administrator interface could be used to transmit a message simultaneously to a single user's computer over the internet using a first industry standard protocol, and to a single user's cellular telephone over a cellular network using a second industry standard protocol. The message sent to the user's computer could be a textual message in English, while the message sent to the user's cellular telephone could be an audio file containing the same message, in Spanish. It is further contemplated that one or more messages can be translated and broadcast in multiple languages, and one or more users can select a language in which to receive a message. A machine translator, such as Systran™ of San Diego, can be used.

User-selected languages or preset languages can be used and saved in data storage so that future messages can be transmitted automatically in selected languages. Use of a translator is beneficial, because not all users in a network may speak the same language, such as in Canada, where a portion of a hydrogen generation network might speak French and another portion of the hydrogen generation network might speak English. This feature ensures smooth and effortless communication between groups of people with language differences and enables the present embodiments to be used simultaneously in multiple countries having different languages.

The present computer instructions can also instruct a processor to receive one or more responses from the hydrogen generation network for regulating hydrogen production. The responses can be transmitted to the administrator interface, stored in the dynamic information database, or combinations thereof. The responses can include a response code from one or more hydrogen generating devices, an "error in response" code indicating insufficient hydrogen generating device information existed to contact one or more hydrogen generating devices, or combinations thereof.

For example, an administrator may transmit a message, individually or simultaneously, using the administrator interface, to multiple hydrogen generating devices in a decentralized hydrogen generation network. This message may activate each of the contacted hydrogen generating devices. Each contacted hydrogen generating device can then transmit a response indicating receipt of the message, information regarding power availability, damage, or natural disaster that may affect power output, or an indication that the message was not received. An error in response code can be received for each message that did not reach an intended hydrogen generating device. The administrator can then selectively transfer power to one or more hydrogen generating devices in response to the information received.

The "error in response" information can also indicate that an e-mail address or phone number is invalid. This error in response information can be noted textually, such as in a report, can be indicated a tone message or another electronic signal indicating no response, or other similar indications.

In an embodiment, the computer instructions can instruct a processor to selectively transfer power from one or more dispatchable or non-dispatchable power sources to one or more hydrogen generating devices using the administrator interface to provide centralized management of hydrogen production. The selective transfer of power can be performed manually, such as by an administrator in response to information obtained through responses from individual hydrogen generating devices, or the transfer of power can be performed automatically, by a processor, such as when responses from hydrogen generating devices exceed a preset setting or indicate a need to transfer or cease transferring power.

It is contemplated that the computer instructions can instruct a processor to receive and store user contact device information relating to one or more user contact devices in the dynamic information database and to transmit messages to one or more associated user contact devices.

User contact devices can include a cellular telephone, a television, a light emitting diode (LED) display, a land phone line, an e-mail address, a fax machine, a pager, a digital display, handheld wireless devices, such as personal digital assistants (PDA) and Blackberries™, and other similar devices.

The one or more users can include individuals, a police department, a school, a fire department, a hospital, a government agency, a military department, a consumer, a business, an association, or combinations thereof. It is also contemplated that users can include owners of hydrogen generating devices.

In an embodiment, the present computer instructions can instruct a processor to associate user contact device information for one or more user contact devices with one or more hydrogen generating devices. This association can be performed to indicate certain users that are owners of hydrogen generating devices, or to denote certain users assigned to use specified hydrogen generating devices.

The computer instructions can further instruct a processor to receive one or more user responses from one or more user contact devices through at least one industry standard protocol. User responses can be transmitted to the administrator interface, stored in the dynamic information database, or combinations thereof. User responses can also include response codes, "error in response" codes indicating insufficient user contact device information existed to contact the a user contact device, or combinations thereof.

Responses can indicate that one or more messages have been successfully received, or responses can indicate a specific need of a user. For example, a user could transmit a response indicating a need for a specific amount of power for a certain hydrogen generating device on a specific date and time.

The administrator interface can include a responder module having a receiver function for receiving responses from user contact devices, hydrogen generating devices, or combinations thereof. The responder module can include an opt-in feature, an opt-out feature, or combinations thereof, for allowing one or more users or administrators to select whether messages and responses are received.

For example, a responder module can include be a software program designed to acknowledge responses that arrive from users, hydrogen generating devices, error in response messages, or combinations thereof, and provide tallies of each response received.

The computer instructions can additionally instruct a processor to receive one or more user messages from one or more user contact devices and transmit the user messages to the administrator interface to disable or enable select hydrogen generating devices on demand.

Users having the ability to disable or enable devices "on demand" are contemplated to have the ability to override another party's ability to control power to the hydrogen generating devices, such as when national security requires home use of a hydrogen generating device to be restricted in favor of military use.

In an embodiment, the present computer instructions can instruct a processor to monitor one or more hydrogen generating devices, manage use of dispatchable or non-dispatchable power sources for tracking power usage by select hydrogen generating devices, and store the tracked power usage in the dynamic information database.

In a contemplated embodiment, the present computer instructions can instruct a processor to assign a priority code to the discretionary power consumption information based on power rates, a classification of one or more hydrogen generating devices, a quantity of power needed by one or more hydrogen generating devices, or combinations thereof. Priority codes can also be assigned to one or more hydrogen generating devices in the hydrogen generation network.

For example, a priority code of "100" can be assigned for users having critical needs, such as hospitals, a priority code of "200" can be used for less critical users, such as grocery stores, a priority code of "300" can be used for a business, and a priority code of "400" can be used for a residence. Specific hydrogen generating devices can also be assigned priority codes.

Power rates can include one or more predetermined fees per kilowatt hour, and a user can be associated with a higher priority code due to a larger required payment per kilowatt hour. It is also contemplated that priority codes can be paired with one or more hydrogen generating devices in the hydrogen generation network.

It is also contemplated that the computer instructions can instruct the processor to receive and store grouping in formation in the dynamic information database. Grouping information can include a geographic zone, a quantity of power consumption for one or more hydrogen generating devices, a transmission capacity of one or more hydrogen generating devices, and combinations thereof. For example, a geographic zone could be "the Gulf Coast region of the United States", the quantity of power consumption needed could be "hospital hydrogen generating device needing 10,000-30,000 kilowatt hours per month". The transmission capacity of the hydrogen generation network can include information such as how much power the can be dispatched to individual hydrogen generating devices per hour, per day, or over another time interval.

In another embodiment, the computer instructions can instruct a processor to receive a cancellation command from the administrator interface for cancelling one or more erroneous messages in progress, or erroneous messages schedule for delivery at a future date and time. The cancellation of messages can also be performed automatically, such as by a processor monitoring available power and cancelling messages indicating availability when preset limits are exceeded.

The present computer instructions can further instruct a processor to transmit a notification to the administrator interface to indicate that one or more messages have been delivered to the hydrogen generation network, a user contact device, or combinations thereof.

The computer instructions for instructing a processor to transmit messages to the hydrogen generation network can also instruct the processor to broadcast messages to one or more hydrogen generating devices or user contact devices at periodic intervals or at a specific date and time. The computer instructions can also instruct the processor to broadcast messages to hydrogen generating devices or user contact devices in a specific geographic area or a disaster zone.

In an embodiment, the present computer instructions can instruct a processor to use one or more security features to control access to the administrator interface, the dynamic information database, any messages or responses, or combinations thereof. Security features can include encryption, a password-protected user account, biometric files, or combinations thereof.

It is further contemplated that the present computer instructions can instruct a processor to generate one or more reports using content in the dynamic information database. The reports can contain response information for one or more messages sent by an administrator, hydrogen generating device information, time and dates, geographic zones to which the report applies, power consumption in view of preset limits and excesses of preset or predefined limits, error in response information, and similar data.

The reports can include a date a message was sent, such as Apr. 2, 2007; a time the message was sent, such as 4:10 pm; a date the message was received, such as Apr. 3, 2007; a time the message was received, such as 4:20 pm, and content of the message, such as "rolling brown out at 2 pm Apr. 4, 2007." Content of the message can be included independent of whether whole or partial message transmission occurred.

In addition the report can include user response information which can include responses, such as "I received the message from the administrator and need assistance in power because I have a security emergency" sent by a user. The report can further include response information, which can include responses from responders attempting to assist users in need, and can also include "error-in-response" information such as a tone or other communication that indicates the message did not reach the intended user contact device or hydrogen generating device.

It is contemplated that the reports can be custom reports, such as a specific type of report containing selected information input by an administrator, or standard reports, such as reports automatically generated by a processor using information in the dynamic information database.

The present computer instructions can be used to contact individuals or hydrogen generating devices, to manage power and hydrogen access among vendors and providers during power outages and emergency conditions, such as storms or fire, and to provide notification of important information, such as thunderstorm warnings, flash flood warnings, tornado warnings, and similar information. Additionally, terrorist threat levels can be transmitted using the present method.

A further benefit of the present embodiments is that users can receive messages on a real-time, instantaneous basis. The present embodiments facilitate a method having a high speed notification and response time, in which information is accessed and stored in a dynamic information database, and can be conveyed to users with user contact devices in a specific priority order. Messages can be conveyed in less than 3 minutes to over 1000 users. Users can be contacted automatically when specific conditions arise, or messages can be transmitted when initiated by an administrator using an administrator interface. Any number of users can be contacted in a systematic manner, and multiple responses can be obtained and stored.

The present embodiments can be used to save lives through the notification of large groups of individuals instantaneously concerning dangerous power outages that may affect critical facilities, military facilities, and hydrogen generating facilities where power outages can result in safety hazards. Messages can be sent to prevent false rumors that a situation is safe. Panic and chaos can be controlled through transmission of one or more consistent messages to a large number of users using the present method.

The present embodiments allow responses from users to be collected so that administrators can send help to users that are in danger, or are experiencing difficulties regarding one or more hydrogen generating devices.

With reference to the figures, FIG. 1 depicts an embodiment of a digital notification and response system utilizing the present computer instructions.

User 20 is depicted within hydrogen generation network 18, in communication with user contact devices 22a and 22b. While user 20 is depicted in communication with two user contact devices, any number of users can be in communication with any number of user contact devices.

FIG. 1 also depicts at least one user 20 in communication with at least one hydrogen generating device 80 which is in communication with the hydrogen generation network 18. It is contemplated that the hydrogen generation network 18 can contain many user contact devices such as over 10,000 users with at least a similar number of hydrogen generating devices.

User contact devices 22a and 22b and the hydrogen generating device 80 can each generate a response 50a-e to the hydrogen generation network 18.

An administrator interface 10, is used for preparing and transmitting messages 12a and 12b, which can be in one or more languages, from an administrator 16 using at least one processor 14a or 14b.

FIG. 1 depicts two processors 14a and 14b, though any number of processors can be used depending on the number of messages, users, and hydrogen generating devices in communication with the administrator interface 10.

Further, while FIG. 1 depicts two messages 12a and 12b, any number of identical messages or different, individualized messages can be sent to any number of individual users.

Administrator interface 10 can be a computer, a cellular telephone, a personal digital assistant, or other similar devices able to input data, messages 12a and 12b, and commands into processors 14a and 14b. The administrator interface 10 can also be a local area network interface, a wide area network interface, a virtual private network interface, a synchronous transfer mode interface, a synchronous optical network interface, a call center, a voice mail, or another similar means to transmit a message to numerous contacts.

The processors 14a and 14b communicate with a dynamic information database 24 stored in data storage 79 in communication with the one or more processors 14a, 14b.

The dynamic information database 24 is used for preparing the messages 12a or 12b and receiving responses 50a, 50b, 50c, and 50d from individual users, or response 50e from hydrogen generating device 80.

Figure 2:
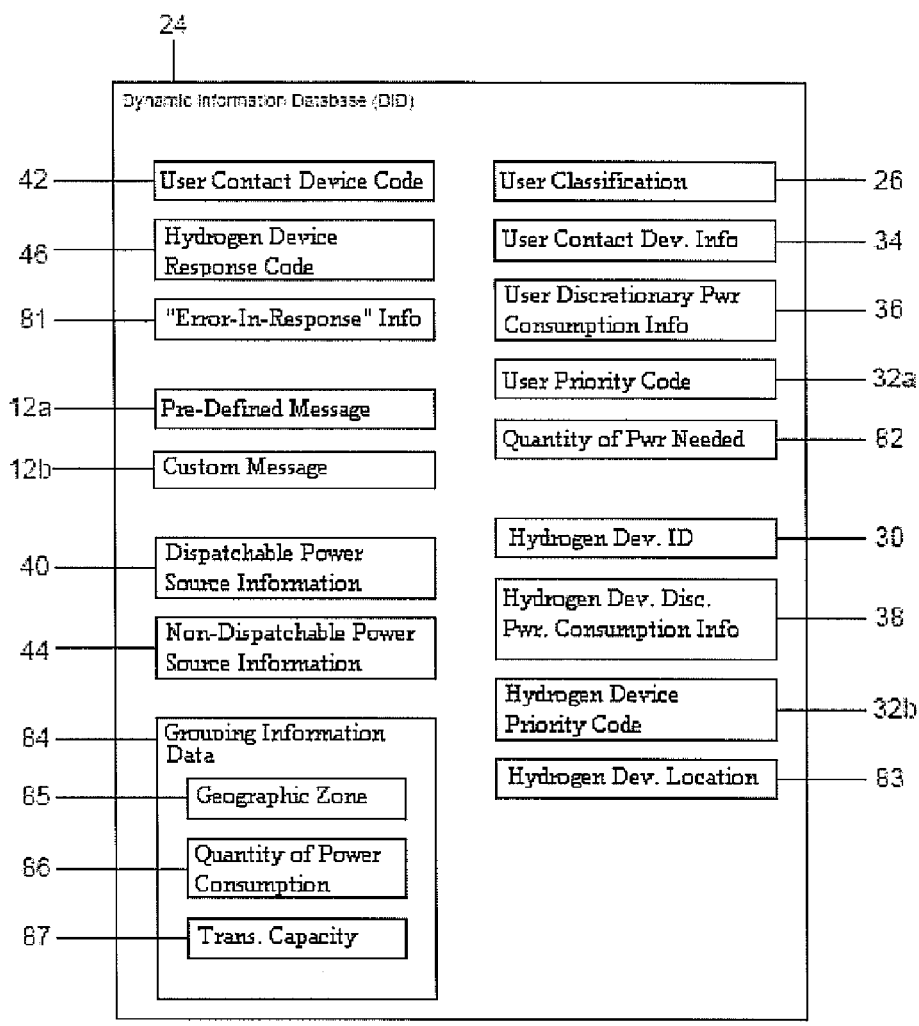
FIG. 2 depicts a representation of an embodiment of a dynamic information database associated with the digital notification and response system of FIG. 1.

The administrator interface 10 initiates distribution of messages 12a and 12b to the hydrogen generation network 18 using information from the dynamic information database 24, namely, grouping information data 84, user contact device information 34, and priority codes for users 32a and priority codes for hydrogen generating devices 32b, depicted in FIG. 2.

The priority codes 32a and 32b can be a priority order that directs the administrator interface 10 to contact a first group of user contact devices, indicated as a first contact. After all of the user contact devices in the first contact have received the message, a priority order can be used to direct the administrator interface 10 to contact a second group of user contact devices, indicated as a second contact. For example, the priority order set by a particular user can include sending an e-mail to a PDA with a defined email address, then calling a home phone number to transmit an audio message, then calling a work phone number. The administrator interface 10 then transmits the message in that priority order. The priority code can be used for a single user, all users in the network, or any intermediate number of users.

In an embodiment, it is contemplated that the administrator interface can continue to contact user contact devices based on the priority order indicated by the users of the system, until all user contact devices are reached, and a response is provided from each user contact device to the dynamic information database. The response from the each user contact device can be "message received," or an individualized message that is actuated by the user.

FIG. 1 depicts administrator interface 10 in communication with a text-to-speech converter 7 and a language translator 52.

In an embodiment the administrator 16 can cancel any messages in progress, or any messages pre-set to be sent on a specific date or time or in the case of a specific event or situation using computer instructions for cancelling a message 92.

Computer instructions 92 can additionally enable administrator 16 to transmit a "disregard message" notification to users that received a message in error, such as when a message is erroneously transmitted or contains erroneous information.

The messages 12a or 12b can be transmitted through one or more industry standard protocols 48a and 48b, individually or simultaneously. Industry standard protocols 48a and 48b can be any type of gateway protocol or similar protocol. Messages 12a and 12b are then received by user contact devices 22a and 22b or hydrogen generating device 80 within the hydrogen generation network 18.

In an embodiment, it is contemplated that the administrator interface 10 can initiate the sending of messages 12a and 12b automatically upon a disaster. For example, if a storm destroys multiple power lines in a specified area, the administrator interface 10 can be notified automatically, and can send the messages 12a and 12b to the appropriate user contact devices of affected users.

In different embodiments, it is contemplated that the messages 12a and 12b can be text messages, numerical messages, one or more images, or combinations thereof. The messages 12a, 12b can be encoded, such as by using encryption means, such as AES 128 or 3DES encryption.

The messages 12a, 12b can include a designation that identifies each messages' importance to all users of the hydrogen generation network 18. Possible designations can include low priority, general priority, significant priority, high priority, and severe priority. The designations can coincide with the US Department of Homeland Security's five-color system. For example, the designations can be color-coded, such as green for a low priority message, blue for a preparedness message or general priority message, yellow for a cautionary message such as a significant priority, orange for an emergency message or high priority message, or red for a critical message with a severe priority. These priority levels can be customized to levels of emergencies, such as the use of red for a category 5 hurricane.

The messages 12a, 12b can be stored on the dynamic information database 24. The messages 12a, 12b can be pre-written messages stored in the dynamic information database 24 for subsequent use by the administrator 16 or can be generated from the dynamic information database 24 based upon inputs from the administrator 16, creating "custom messages" that can be transmitted using the administrator interface 10.

The administrator interface 10 can also include a "call me" feature 13. The "call me" feature 13 enables an administrator 16 to compose a message to send to members of the hydrogen generation network 18.

FIG. 1 also depicts computer instructions to notify the administrator 93 disposed within the data storage 79 to advise the administrator 16 regarding available dispatchable and non-dispatchable power and upcoming usage needs, and notifying the administrator 16 regarding whether messages 12a, 12b reached their intended users. Additionally FIG. 1 shows computer instructions in the data storage 79 for broadcasting 94 as described above. Computer instructions for generating reports 95 can also be contained in the data storage 79.

The administrator interface 10 can further include a responder module 96, as described previously, and a security feature 97.

The responder module 96 can include computer instructions that enable a receiver function to receive responses from various users that reply to messages and/or a storage function for recording received responses in audio files, a dual-tone multi-frequency "DTMF", and/or an interactive voice response "IVR" format.

In an embodiment, the responder module can have a reporting function for providing the status of the responses to the administrator. The information obtainable through reporting function can be protected using security access features which can include encryption, a user log in with password, or a biometric file. The security access features can also include a bar code reader, a radio frequency identification device "RFID" tag reader, a scannable badge reader, a security token, a smart card reader, a magnetic card reader, and combinations thereof.

FIG. 2 shows a schematic depiction of the dynamic information database 24. The dynamic information database 24 can be a SQL™ database, MySQL™ database or other industry standard databases, an Oracle™ database, or other similar databases that can organize information in a similar manner.

It is contemplated that the dynamic information database 24 can be resident in data storage 79 in communication with processors 14a and 14b. The dynamic information database 24 contains a user classification 26, such as a type of facility or individual, for each user, such as user 20, depicted in FIG. 1.

For example, a user facility can contain a hydrogen generating device 80, and each such facility can have a related user classification. For example, a hospital can have a hydrogen generating device and be classified as a "critical care" facility, which can require constant power. In contrast, a residential user can be classified as "evening status," and receive power for a hydrogen generating device only in the evening after work hours.

Classifications and priorities can be assigned based on status, such as an emergency care provider, a high end residency, a military operation facilities, a homeland security facility, a critical governmental facility, a general public facility, a communication network, a traffic system, a public broadcast system, and other similar systems.

User contact device information 34 is also included in dynamic information database 24 and can include an e-mail address, an internet protocol (IP) address, a phone number, and combinations thereof. User contact information 34 can further include the user's name, the user's address, the user's phone number, the user's device address, the user's social security number, an account code, and combinations thereof. Each user contact device can include information that is unique to each individual user contact device or can include information that is common to all contact devices. For example, a serial number for a cellular phone, a Mac address for an Ethernet card, and other telecommunication device information can be included in dynamic information database 24.

Additionally, dynamic information database 24 contains hydrogen generating device identification 30 such as an identification code, an address, a phone number, a social security number of users at the hydrogen generating device 80, a tax identification number, a bank account, or combinations thereof, for each hydrogen generating device 80 in the hydrogen generation network. Similar information can be stored in the dynamic information database 24 relating to each user within the network such as dispatchable power source information 40, and non-dispatchable power source information 44. Hydrogen generating device identification 30 can include information sufficient for the administrator interface 10 to transmit messages and receive response from related hydrogen generating devices.

Dynamic information database 24 can include user discretionary power consumption information 36 for at least one user of the hydrogen generation network, which can be an amount of power that at least one user requires during a time interval that can be determined by an administrator, such as 4 hours, 8 hours, 2 hours every Sunday, or 3 hours on "date" night. The dynamic information database 24 can also contain discretionary power consumption information of each hydrogen generating device in the network.

It is additionally contemplated that the discretionary power consumption information can be assigned a priority code based on power rates. Alternatively, one or more users can have a classification code which indicates a quantity of power needed by a user. For example, power rates can be set at one or more predetermined fees per kilowatt hour, and a user can be associated with a higher priority code because of higher payment per kilowatt hour.

Non-dispatchable power source 40 can relate to a wind power facility, a solar powered facility, or an intermittent water supply hydroelectric facility for providing electricity. Dispatchable power source information 44 can relate to a hydroelectric power plant, a hydrocarbon based electrical production facility, a nuclear power plant, a geothermal power generation facility, a bank of batteries, at least one capacitor, at least one fuel cell, or a tidal power generator using ocean tides, which provides electricity to the user or the hydrogen generating device.

The dynamic information database 24 can include response codes from user contact devices 42, and response codes from hydrogen generating devices 46, relating to responses received from a user, or a hydrogen generating device.

"Error-in-Response" information 81 can also be tracked by the database 24. Error in response information can relate to failed attempts to transmit a message to a user contact device or to a hydrogen generating device. Error in response codes can be received when insufficient user contact device information exists to contact a user contact device or insufficient hydrogen generating device information exists to contact a hydrogen generating device. Error in response data and response data provides the administrator with knowledge whether or not one or more messages have reached the intended recipients.

The "Error-in-Response" information 81 can also indicate that an e-mail address or phone number is invalid. This Error-in-Response information can be noted in the report as an invalid number, and can be indicated a tone message or another electronic signal indicating no response.

The dynamic information database 24 can also include information regarding the amount of power needed by a particular user 82 and information regarding the hydrogen generating device location 83.

Grouping information 84 of the dynamic information database 24, can include geographic zones 85, quantity of power consumption for a group of users 86, and transmission capacity of the network 87.

Figure 3:
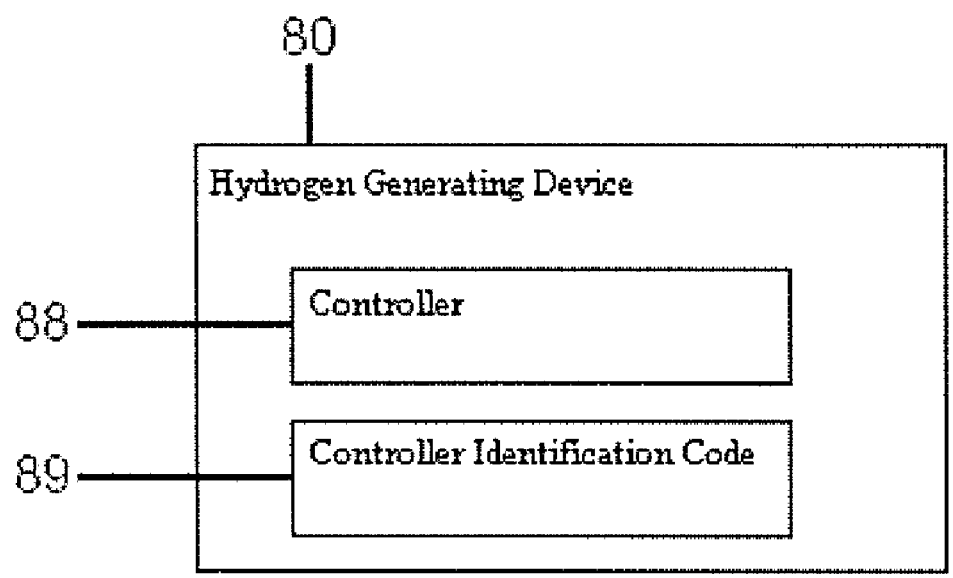
FIG. 3 depicts a representation of an embodiment of a hydrogen generating device.

It is further contemplated that the hydrogen generating device 80 can include at least two elements shown in FIG. 3, namely, a controller 88, a controller identification code 89, or combinations of these items.

The dynamic information database can store one or more responses and unique address of each user contact device. Responses can be audio files or dual-tone multi-frequency "DTMF" tones, also known as touch tones. The "DTMF" tone can be used for telephone signaling over a line in a voice frequency band to a call switching center. The response from the user contact device can also be a text telephone such as "TTY" communication, including teletype communication, or a time division duplex (TDD) communication.

The embodiments have been described in detail with particular reference to certain preferred embodiments, thereof, but it will be understood that variations and modifications can be effected within the scope of the embodiments, especially to those skilled in the art.

What is claimed is:

1. Computer instructions in communication with at least one processor having data storage, wherein the at least one processor is in communication with a hydrogen generation network comprising at least one hydrogen generating device, and wherein the computer instructions instruct the at least one processor to:
   form a dynamic information database in the data storage;
   receive and store a member of the group consisting of: at least one hydrogen generating device identification for the at least one hydrogen generating device, discretionary power consumption information of the at least one hydrogen generating device, or combinations thereof in the dynamic information database;
   receive and store a member of the group consisting of: dispatchable power source information for at least one dispatchable power source, non-dispatchable power source information for at least one non-dispatchable power source, or combinations thereof in the dynamic information database;
   receive at least one message from an administrator interface, wherein the administrator interface is in communication with the at least one processor;
   transmit the at least one message to the hydrogen generation network through at least one industry standard protocol, wherein the at least one message activates the at least one hydrogen generating device, deactivates the at least one hydrogen generating device, manages decentralized storage of hydrogen, or performs combinations thereof;
   receive at least one response from the hydrogen generation network for regulating hydrogen production; and
   store the at least one response in the dynamic information database.

2. The computer instructions of claim 1, further comprising computer instructions for instructing the at least one processor to selectively transfer power from at least one dispatchable power source, at least one non-dispatchable power source, or combinations thereof for providing centralized management of hydrogen production using the administrator interface.

3. The computer instructions of claim 1, further comprising computer instructions for instructing the at least one processor to:
    receive and store user contact device information for at least one user contact device in the dynamic information database, wherein the at least one user contact device is in communication with the administrator interface; and
    transmit the at least one message to the at least one user contact device.

4. The computer instructions of claim 3, further comprising computer instructions for instructing the at least one processor to:
    receive at least one user response from the at least one user contact device through the at least one industry standard protocol; and
    transmit the at least one user response to the administrator interface, store the at least one user response in the dynamic information database, or combinations thereof.

5. The computer instructions of claim 4, further comprising computer instructions for instructing the at least one processor to:
    receive at least one user message from the at least one user contact device; and
    transmit the at least one user message to the administrator interface to disable or enable the at least one hydrogen generating device on demand.

6. The computer instructions of claim 4, further comprising computer instructions for instructing the at least one processor to receive: a user response code from the at least one user contact device, an user "error in response" code that indicates insufficient user contact device information existed to contact the at least one user contact device, or combinations thereof.

7. The computer instructions of claim 3, further comprising computer instructions for instructing the at least one processor to associate the user contact device information with the at least one hydrogen generating device.

8. The computer instructions of claim 3, wherein the computer instructions for instructing the at least one processor to transmit the at least one message to the at least one user contact device instruct the at least one processor to broadcast the at least one message to a member of the group consisting of: the at least one user contact device at periodic intervals, the at least one user contact device in a defined geographic area, the at least one user contact device in a designated disaster zone, the at least one user contact device at a specific date and time, and combinations thereof.

9. The computer instructions of claim 1, further comprising computer instructions for instructing the at least one processor to:
    monitor the at least one hydrogen generating device;
    manage use of the at least one dispatchable power source, the at least one non-dispatchable power source, or combinations thereof;
    track power usage by the at least one hydrogen generating device, forming tracked power usage; and
    store the tracked power usage in the dynamic information database.

10. The computer instructions of claim 1, further comprising computer instructions for instructing the at least one processor to receive: a response code from the at least one hydrogen generating device, an "error in response" code that indicates insufficient hydrogen generating device information existed to contact the at least one hydrogen generating device, or combinations thereof.

11. The computer instructions of claim 1, further comprising computer instructions for instructing the at least one processor to assign a priority code to the discretionary power consumption information based on a member of the group consisting of: power rates, a classification of the at least one hydrogen generating device, a quantity of power needed by the at least one hydrogen generating device, or combinations thereof.

12. The computer instructions of claim 1, further comprising computer instructions for instructing the at least one processor to receive and store in the dynamic information database, a hydrogen generating device location for the at least one hydrogen generating device.

13. The computer instructions of claim 1, further comprising computer instructions for instructing the at least one processor to receive and store grouping information in the dynamic information database.

14. The computer instructions of claim 1, further comprising computer instructions for instructing the at least one processor to receive a cancellation command from the administrator interface for cancelling: at least one erroneous message in progress, at least one erroneous message scheduled for delivery at a future date and time, or combinations thereof.

15. The computer instructions of claim 1, further comprising computer instructions for instructing the at least one processor to transmit a notification to the administrator interface when the at least one message has been delivered to the hydrogen generation network.

16. The computer instructions of claim 1, wherein the computer instructions for instructing the at least one processor to transmit the at least one message to the hydrogen generation network instruct the at least one processor to broadcast the at least one message to a member of the group consisting of: the at least one hydrogen generating device at periodic intervals, the at least one hydrogen generating device in a defined geographic area, the at least one hydrogen generating device in a designated disaster zone, the at least one hydrogen generating device at a specific date and time, and combinations thereof.

17. The computer instructions of claim 1, further comprising computer instructions for instructing the at least one processor to activate at least one security feature to control access to the administrator interface, the dynamic information database, the at least one message, the at least one response, or combinations thereof.

18. The computer instructions of claim 1, further comprising computer instructions for instructing the at least one processor to generate at least one report using content in the dynamic information database.

19. The computer instructions of claim 1, further comprising computer instructions for instructing the at least one processor to convert the at least one message from text to a sound file.

20. The computer instructions of claim 1, further comprising computer instructions for instructing the at least one processor to assign at least one priority code for at least one hydrogen generating device.

* * * * *